(12) United States Patent
Zhang et al.

(10) Patent No.: US 9,231,383 B2
(45) Date of Patent: Jan. 5, 2016

(54) CORONA DISCHARGE ASSEMBLY, ION MOBILITY SPECTROMETER, COMPUTER PROGRAM AND COMPUTER READABLE STORAGE MEDIUM

(71) Applicant: NUCTECH COMPANY LIMITED, Beijing (CN)

(72) Inventors: Qingjun Zhang, Beijing (CN); Yuanjing Li, Beijing (CN); Zhiqiang Chen, Beijing (CN); Yanchun Wang, Beijing (CN); Ziran Zhao, Beijing (CN); Yinong Liu, Beijing (CN); Yaohong Liu, Beijing (CN); Xiang Zou, Beijing (CN); Qiufeng Ma, Beijing (CN); Junxiao Wang, Beijing (CN); Jianping Chang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 14/578,326

(22) Filed: Dec. 19, 2014

(65) Prior Publication Data
US 2015/0188296 A1 Jul. 2, 2015

(30) Foreign Application Priority Data
Dec. 30, 2013 (CN) .......................... 2013 1 0742038

(51) Int. Cl.
*H01J 49/00* (2006.01)
*H01T 19/00* (2006.01)
*H01J 49/16* (2006.01)
*G01N 27/62* (2006.01)

(52) U.S. Cl.
CPC .............. *H01T 19/00* (2013.01); *G01N 27/622* (2013.01); *H01J 49/168* (2013.01)

(58) Field of Classification Search
None
See application file for complete search history.

(56) References Cited

U.S. PATENT DOCUMENTS

| 3,873,835 | A | * | 3/1975 | Ignatjev | H01T 23/00 250/324 |
| 4,041,922 | A | * | 8/1977 | Abe | F02B 19/12 123/143 B |
| 4,363,072 | A | * | 12/1982 | Coggins | H01T 23/00 250/324 |
| 5,485,016 | A | * | 1/1996 | Irie | H01J 49/0422 250/281 |
| 5,726,447 | A | * | 3/1998 | Aisawa | H01J 49/145 250/288 |
| 5,768,087 | A | * | 6/1998 | Vernitskiy | H01T 23/00 15/256.5 |
| 6,349,668 | B1 | * | 2/2002 | Sun | B05B 5/00 118/723 E |

(Continued)

FOREIGN PATENT DOCUMENTS

CA 2214344 6/1993

*Primary Examiner* — Andrew Smyth
(74) *Attorney, Agent, or Firm* — McDermott Will & Emery LLP

(57) ABSTRACT

The present invention discloses a corona discharge assembly, including: an ionization discharge chamber, wherein the ionization discharge chamber includes a metal corona cylinder, and the metal corona cylinder is provided with an inlet of a gas to be analyzed and an annular piece-shaped port which forms a non-uniform electric field with corona pins and is provided with a circular hole at the middle; a rotating shaft is installed on the cylinder wall of the metal corona cylinder in an insulating manner, the rotating shaft is vertical to the axial line of the metal corona cylinder, and a turntable provided with multiple corona pins at the outer edge is installed at the end part of the rotating shaft the axial line of the metal corona cylinder passes in parallel through the rotation plane of the turntable. The present invention further discloses an ion mobility spectrometer using the above-mentioned corona discharge assembly.

16 Claims, 6 Drawing Sheets

(56) References Cited

U.S. PATENT DOCUMENTS

| | | | |
|---|---|---|---|
| 7,326,926 B2* | 2/2008 | Wang | H01J 49/16 250/288 |
| 2002/0017605 A1* | 2/2002 | Jenkins | H01J 49/12 250/287 |
| 2002/0125423 A1* | 9/2002 | Ebeling | H01J 49/044 250/288 |
| 2004/0035128 A1* | 2/2004 | Kaji | A61L 9/22 62/264 |
| 2004/0089802 A1* | 5/2004 | Kato | H01J 49/145 250/285 |
| 2007/0103842 A1* | 5/2007 | Partridge | B03C 3/09 361/220 |
| 2007/0235661 A1* | 10/2007 | Gefter | H01T 23/00 250/424 |

* cited by examiner

CORONA DISCHARGE ASSEMBLY, ION MOBILITY SPECTROMETER, COMPUTER PROGRAM AND COMPUTER READABLE STORAGE MEDIUM

CROSS-REFERENCE TO RELATED APPLICATION

This application claims priority to and the benefit of Chinese Patent Application No. 201310742038.1 filed in the State Intellectual Property Office of the P.R.C (SIPO) on Dec. 30, 2013, the entire contents of which are incorporated herein by reference.

TECHNICAL FIELD

The present invention relates to the filed of security detection technology, in particular, to a multi-pin corona discharge assembly, which is convenient to manufacture and is long in service life, an ion mobility spectrometer used for detecting narcotics and explosives and utilizing the assembly as an ionization source, corresponding computer program and computer readable storage medium.

BACKGROUND

An ion mobility spectrometer resolves ions according to different drift velocities of different ions under a uniform weak electric field. It has the advantages of high resolution speed, high sensitivity, free of a vacuum environment and convenience for miniaturization, thus being widely applied to the detection field of narcotics and explosives. A typical ion mobility spectrometer is generally composed of a sample introduction part, an ionization part, an ion gate, a migration area, a collection area, a readout circuit, a data collecting and processing part, a control part and the like. Wherein the main function of the ionization part is to transform sample molecules into ions for migration and separation, thus the ionization effect has very direct influence on the performance of the spectrometer. In the prior art, the most common and most widely used ionization assembly is a $^{63}$Ni radioactive source, which has the advantages of small volume, high stability and no an additional circuit, but also has the problems of narrow linear range, low ion transformation concentration and radiation pollution. Especially, the radiation pollution problem brings a lot of inconvenience to operation, transportation and management of equipment. In order to overcome the above-mentioned problems, corona discharge technology is adopted to replace radioactive source technology. Corona discharge refers to a phenomenon of gas molecule separation induced by a local strong electric field in a non-uniform electric field in the space. Ions directly generated by corona discharge are generally called reactant ions, when sample molecules with higher protons or electron affinity pass by the ionization area, the sample molecules capture the charges of the reactant ions to be ionized. In general, a corona discharge structure is relatively simple, so the cost is low; meanwhile, the concentration of charges generated by corona discharge is much higher than that of the radioactive source, thereby being beneficial to improving the sensitivity of the ion mobility spectrometer and obtaining a larger dynamic range. Application examples of corona discharge serving as the ionization source of the ion mobility spectrometer are reported in patents U.S. Pat. No. 5,485,016 and CA2124344 and CN1950698A. A common corona discharge structure has a discharge form of pinpoint-flat plate or pinpoint-cylinder, as shown in FIGS. 1A and 1B. The fixed tail end of a corona pin realizing discharge is usually installed on a supporting matrix, and the tail end is connected to a high voltage power supply; the other end of the corona pin is a free end (i.e., a pinpoint) and is generally a tip with a very small radius of curvature (smaller than 0.1 mm) A non-uniform electrostatic field is formed in the space between a flat or cylindrical electrode and the pinpoint, such that the electric field intensity near the pinpoint is very high, and the electric field intensity of the space away from the pinpoint progressively decreases. Gas ionization only occurs in the space close to the surface of the free tip of the electrode, the ionization area is very small, thus the generated ion concentration is quite small as well; if the ionization area is increased, a higher voltage is needed, and the requirement on the high voltage power supply is very high. In addition, under the condition that only one tip discharges, the corona discharge will generate oxidation on a corona electrode, after long term operation, chemical reactions resulting from water vapor or the like in the gas will severely corrode the tip to increase the radius of curvature thereof, thus increasing the voltage threshold of the corona discharge, reducing the corona discharge stability and leading to the end of service life; furthermore, in order to achieve a smaller radius of curvature, the diameter of the pin is very small in general, the strength is quite low, thus it is very difficult to keep a higher position precision during manufacture and assembly of a product. In order to improve this situation, a multi-pin corona discharge structure is developed.

U.S. Pat. No. 7,326,926B2 describes a typical multi-pin cluster corona discharge ion source, as shown in FIG. 1C. A cluster of parallel corona pins is adopted to replace a single corona pin of the typical corona discharge ion source; due to the design of simultaneously loading a high voltage on multiple tips of the multi-pin cluster to discharge, the problem of reduced service life of the ionization source caused by discharge failure of the single corona pin is eased to a certain degree. However, the design of simultaneously loading the high voltage on the multiple tips to discharge also has obvious disadvantages. Firstly, the high voltage is simultaneously loaded on multiple pins, electric fields formed by the pins will influence each other to reduce the electric field intensity at the pinpoints, thus a corona voltage needs to be improved, as a result, a higher requirement is proposed on the high voltage power supply; in addition, due to the processing inconsistency, the shapes and surface conditions of the tips are different, all tips cannot be guaranteed to meet a corona discharge condition, the pin with a relatively small radius of curvature firstly discharges and is gradually corroded to result in gradual increasing the radius of curvature thereof to fail to meet the corona discharge condition, and the rest pins meeting the condition begin to discharge, in this case, how many pins generate corona discharge at a moment cannot be guaranteed, with high stochastic property, so that the change of the number of ions generated by ionization is very large, resulting in unstable corona discharge, which is not conducive to the stable work of the ion mobility spectrometer.

SUMMARY

The inventor realizes that, if alternate corona discharge of multiple pins can be achieved, namely, at a moment, the electric field intensity at the pinpoint of only one pin meets a corona discharge threshold, and the electric field intensity at the pinpoints of the other pins is lower or is zero, the problems of instability of a corona ion source caused by simultaneously loading a high voltage on the multiple pins and a short service life of a single-pin corona ion source can be solved at the same time.

The object of the present invention is to provide a design solution of a turntable-controlled multi-pin alternate corona discharge assembly, which is stable and is convenient to operate, and the design can be used for effectively prolonging the overall service life of an ionization assembly, conductive to improving the ion pass rate, reducing the dissipation of ions in a corona cavity, improving the stability of corona discharge of an ion source and improving the performance of a mobility spectrometer.

In order to achieve the above-mentioned purpose, according to the embodiment of the present invention, the corona discharge assembly includes an ionization discharge chamber, wherein the ionization discharge chamber includes a metal corona cylinder, and the metal corona cylinder is provided with an inlet of a gas to be analyzed and an ion exit which forms a non-uniform electric field with corona pins and is provided with a circular hole at the middle; a rotating shaft is installed on the cylinder wall of the metal corona cylinder in an insulating manner, the rotating shaft is vertical to the axial line of the metal corona cylinder, and a turntable provided with multiple corona pins at the outer edge is installed at the end part of the rotating shaft, the axial line of the metal corona cylinder passes in parallel through the rotation plane of the turntable. Therefore, alternate corona discharge of the multiple pins can be achieved, namely, at a moment, the electric field intensity at the pinpoint of only one pin reaches the corona discharge threshold, and the electric field intensity at the pinpoints of the other pins is lower or is zero, and the problems of instability of the corona ion source caused by simultaneously loading the high voltage on the multiple pins and the short service life of the single-pin corona ion source can be solved at the same time.

Preferably, the turntable is contained in a sealed metal shielding cylinder, and the metal shielding cylinder includes a trumpet-shaped focusing electrode used for forming a gathered static electric field.

Preferably, the metal corona cylinder and the sealed metal shielding cylinder are arranged coaxially.

Preferably, a narrow slit is formed on the focusing electrode, for pass of the corona pins when rotating. The turntable is driven by the rotating shaft to expose a certain corona pin from the narrow slit by rotating (at this time, the corona pin is called a main corona pin), and to locate at a position matching with the electrode at the ion exit of the corona cylinder (the main corona pin is overlapped with the axial line of the corona cylinder port and the axial line of the trumpet-shaped opening of the focusing electrode, at this time, the pinpoint of the corona pin is closest to the ion exit of the corona cylinder), in order to generate corona discharge; the rest pins are contained in the metal shielding cylinder with the same potential to fail to generate the corona discharge.

Preferably, the multiple corona pins are electrically interconnected. By adopting the multiple electrically interconnected corona pins, the multiple corona pins do not need to be singly provided with respective current paths, so that the fabrication process is simplified; moreover, since expect the main corona pin, the rest corona pins are located in the metal shielding cylinder, this arrangement will not cause the rest corona pins to generate unexpected corona discharge.

Preferably, the corona discharge assembly further includes an ion reaction and storage ring which is an internal passage with a structure like a trumpet, wherein the ion reaction and storage ring is not in electrical contact with the metal corona cylinder, and the large opening end of the ion reaction and storage ring is in contact with a first grid of an ion gate to form an equipotential area between the interior of the large opening end and the first grid of the ion gate, in order to store ions. Therefore, the ions generated by corona discharge can enter an ion reaction and storage area under the traction of the electric field. The main functions of the ion reaction and storage ring are as follows: when the ion gate is closed, ensuring full reaction and compound between primary action ions and a sample gas and generating and storing a characteristic ion cluster to be detected; and when the ion gate is open, focusing the compounded ion cluster and driving the ion cluster to enter an ion migration cavity through the ion gate. By means of the design, corona discharge impulse interference can be effectively shielded, the fluctuation of the number of the ions caused by corona impulse is shielded, the pass rate of the ions at the ion gate is increased, and an effect of stabilizing an ion mobility spectrum line is achieved.

According to the embodiment of the present invention, an ion mobility spectrometer is further disclosed, the ion mobility spectrometer includes: the above-mentioned corona discharge assembly; an ion gate, wherein the ion gate is composed of two opposite grids; a migration area, wherein the migration area includes drift electrodes, the drift electrodes are concentric equidistant circular ring electrodes, the potentials of the circular ring electrodes changing at an equal difference, in order to form a traction electric field so that the ions move towards the direction of a Faraday disc; and, the Faraday disc being a circular flat plate, the rear of which is connected with a charge sensitive amplifier to read ion signals.

Due to the structural features of the corona discharge assembly according to the present invention, at any moment, only one corona pin rotates to the position closest to the ion exit of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, the multiple pins alternatively locate at a corona discharge position to discharge due to the rotation of the turntable, thus compared with a single-pin structure, the structure can be used for prolonging the service life of the integral corona discharge assembly; meanwhile, due to the focusing function of the focusing electrode, the pass rate of the ions can be increased, the dissipation of the ions in the corona cylinder and the ion reaction and storage ring is reduced, more ions generated within a unit time can enter the ion migration area; the sensitivity of the ion mobility spectrometer is beneficially improved; since the multiple corona pins are fixed on the turntable, during installation, the position of the electrode can be accurate and stable, thus mass manufacture is easier to achieve.

DETAILED DESCRIPTION OF THE EMBODIMENTS

To make the objective, structures and advantages of the present invention clearer, the present invention will be further described as below in details with reference to the accompanying drawings. The embodiments below are described for illustration only, not for limiting the scope of the invention.

Figure 1A:
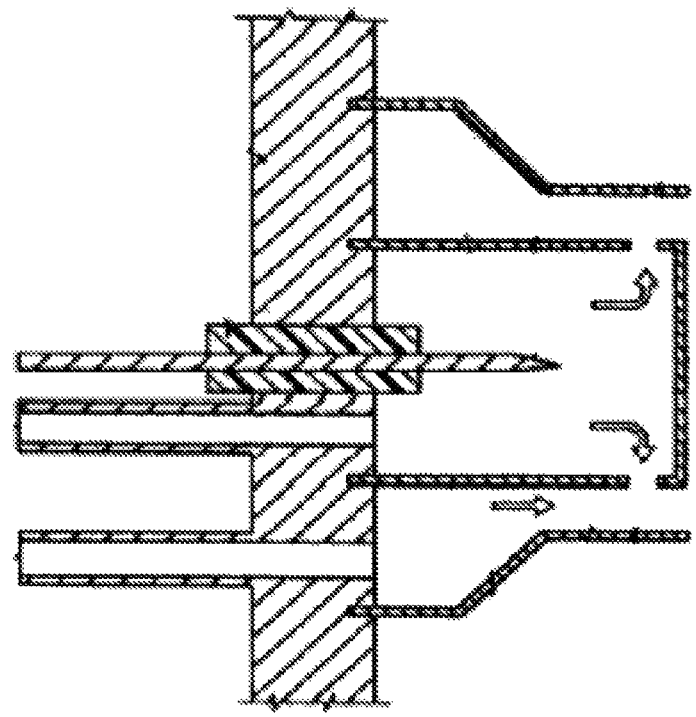
FIGS. 1A, 1B and 1C are schematic diagrams of a structure of a traditional corona discharge structure.
Figure 1B:
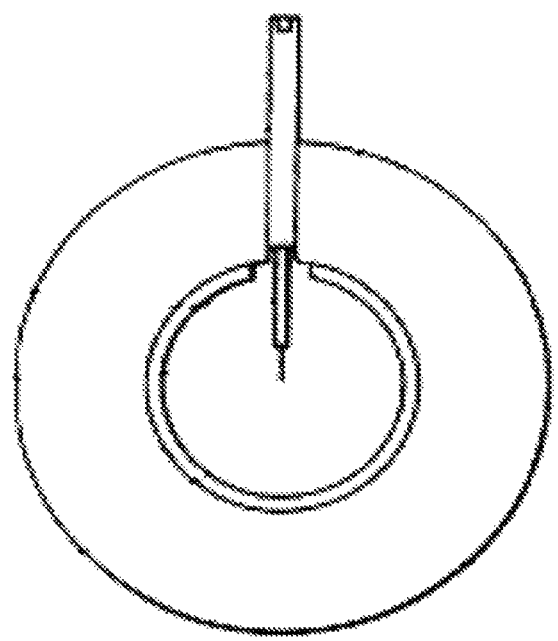
Figure 1C:
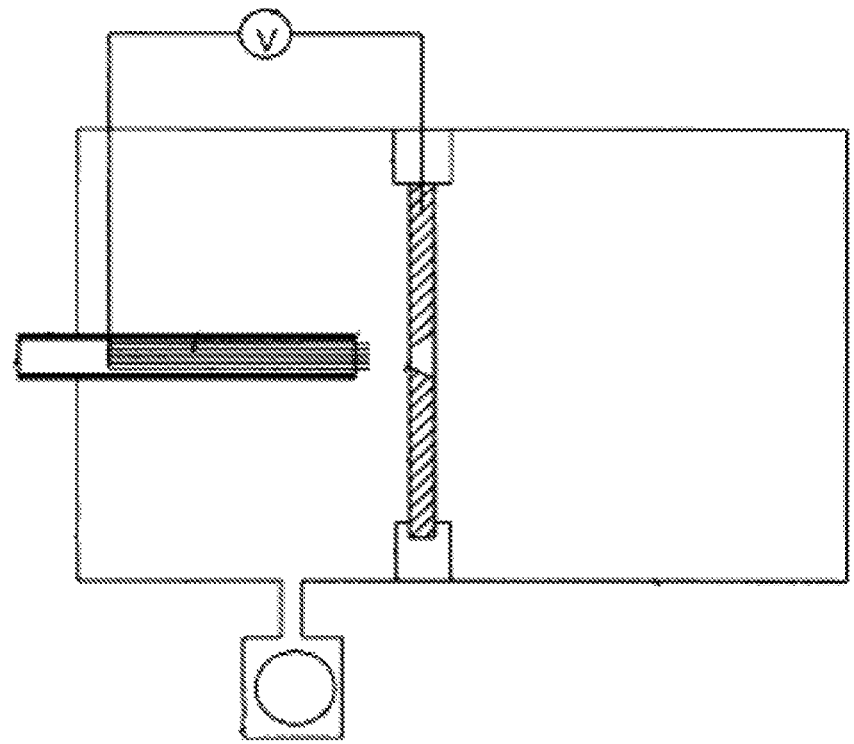
Figure 2A:
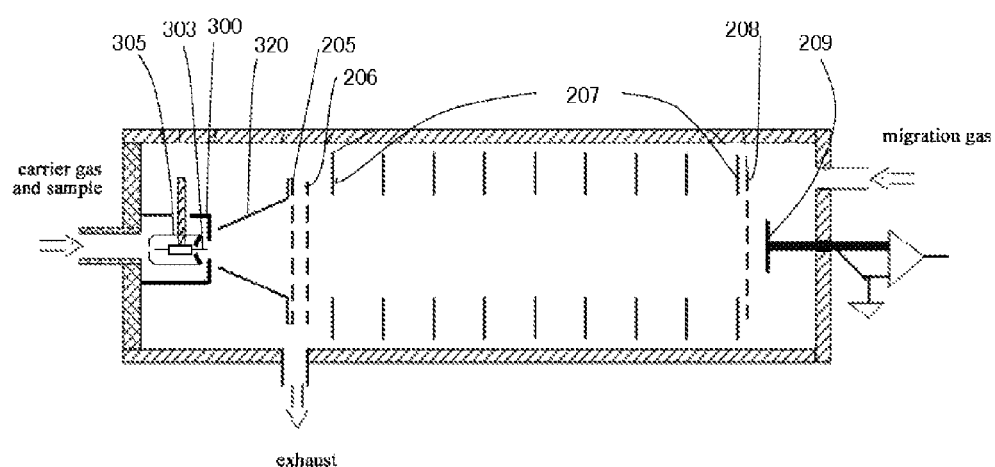
FIG. 2A is a schematic diagram of a structure of an ion mobility spectrometer using a corona discharge ion source of a turntable with multiple corona pins according to an embodiment of the present invention.

In the corona discharge ion mobility spectrometer as shown in FIG. 2A, a non-uniform electric field achieving corona discharge is mainly formed by a main corona pin 303 located on the axial line of a corona cylinder 300 of a turntable, a focusing electrode 308, the corona cylinder 300 and an ion reaction and storage ring 320. The ion mobility spectrometer includes: a corona discharge assembly; an ion gate composed of two opposite grids 205, 206; a migration area, wherein the migration area includes drift electrodes 207, and the drift electrodes 207 are concentric equidistant circular ring electrodes; and a Faraday disc 209, the rear of which is connected with a charge sensitive amplifier to read ion signals.

According to the embodiment of the present invention, the corona discharge assembly includes an ionization discharge chamber, wherein the ionization discharge chamber includes a metal corona cylinder 300, and the metal corona cylinder 300 is provided with an inlet of a gas to be analyzed and an ion exit which forms a non-uniform electric field with the corona pins 303 and is provided with a circular hole at the middle; a rotating shaft 304 is installed on the cylinder wall of the metal corona cylinder 300 in an insulating manner, the rotating shaft 304 is vertical to the axial line of the metal corona cylinder 300, and the turntable provided with multiple corona pins at the outer edge is installed at the end part of the rotating shaft 304. The axial line of the metal corona cylinder passes in parallel through the rotation plane of the turntable.

Therefore, alternate corona discharge of multiple pins can be achieved, namely, at a moment, the electric field intensity at the pinpoint of only one corona pin 303 reaches the corona discharge threshold, and the electric field intensity at the pinpoints of the other pins is lower or is zero, and the problems of instability of a corona ion source caused by simultaneously loading a high voltage on multiple pins and a short service life of a single-pin corona ion source can be solved at the same time.

Figure 2B:
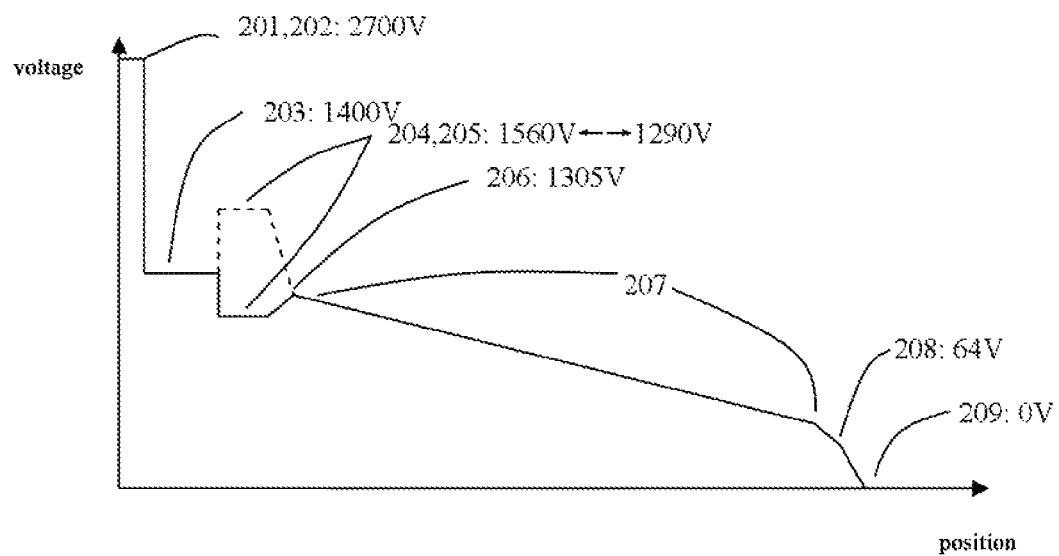
FIG. 2B is a schematic diagram of potentials of electrodes of the ion mobility spectrometer in FIG. 2A under a forward mode.
Figure 3A:
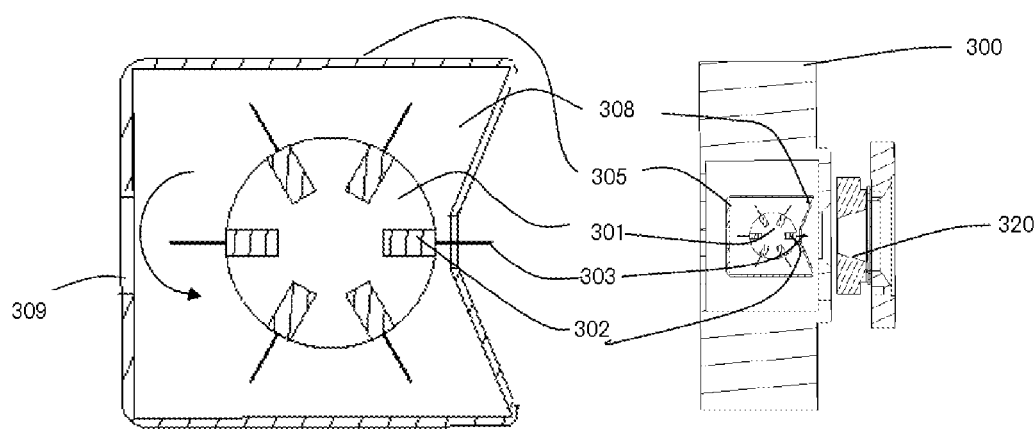
FIG. 3A is a top view of structures of a turntable with multiple corona pins and a focusing electrode according to an embodiment of the present invention.
Figure 3B:
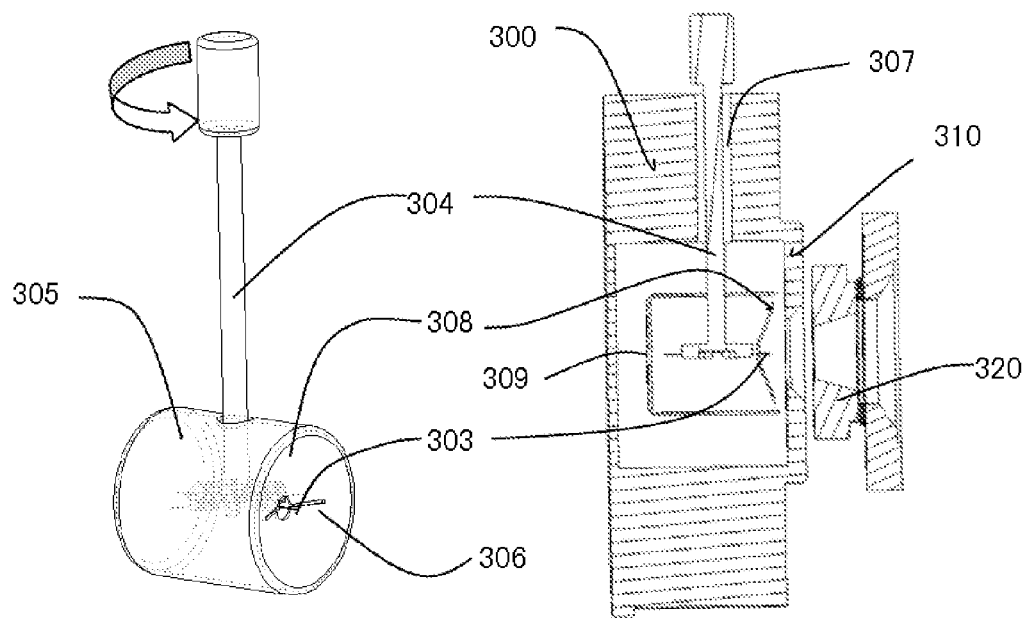
FIG. 3B is a schematic diagram and a side view of structures of the turntable with multiple corona pins and the focusing electrode according to the embodiment of the present invention.
Figure 4A:
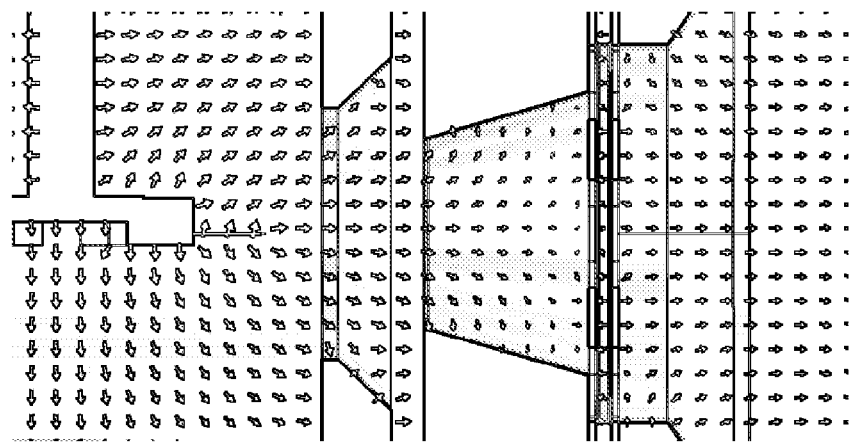
FIG. 4A is a simulated diagram of an electric field direction of an ion source in the absence of a focusing electrode.
Figure 4B:
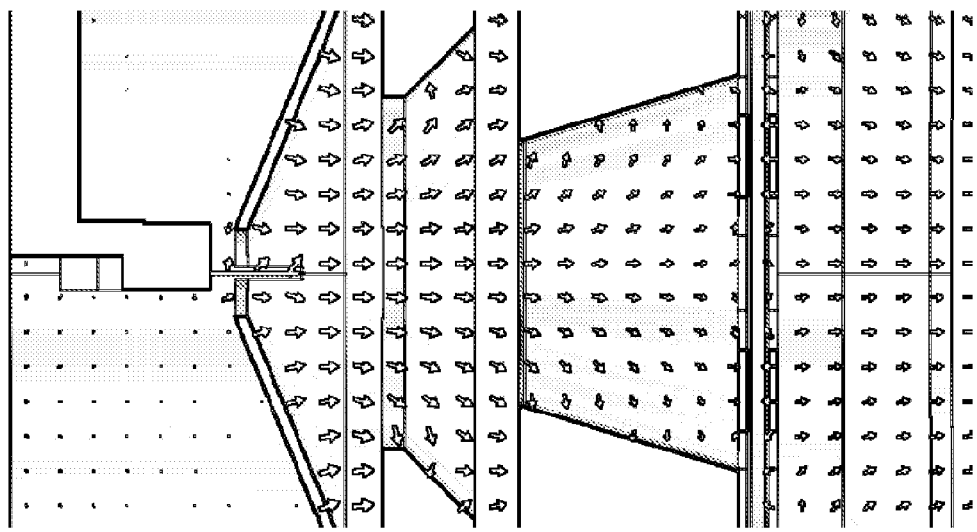
FIG. 4B is a simulated diagram of an electric field direction of an ion source in the presence of a focusing electrode.
Figure 4C:
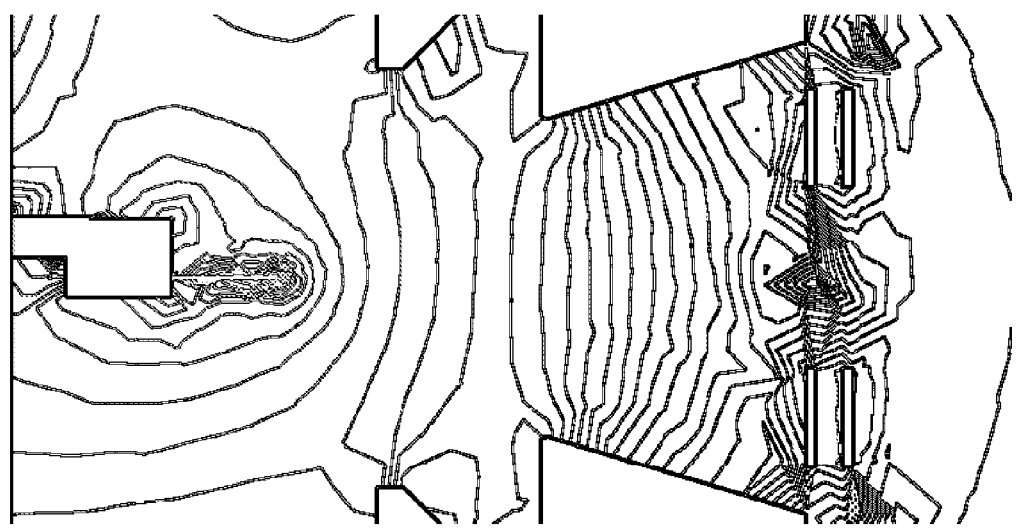
FIG. 4C is a simulated diagram of an equipotential line of an ion source in the absence of a focusing electrode.
Figure 4D:
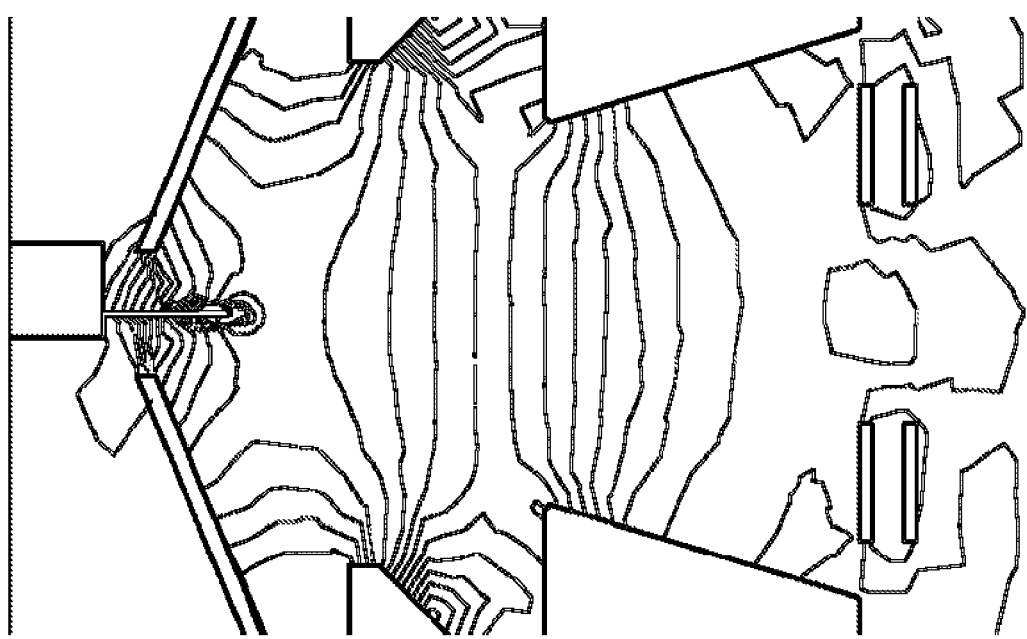
FIG. 4D is a simulated diagram of an equipotential line of an ion source in the presence of a focusing electrode.

FIG. 2B is a schematic diagram of potentials of electrodes of the ion mobility spectrometer in FIG. 2A under a forward mode. FIG. 3A is a top view of structures of a turntable with multiple corona pins and a focusing electrode according to an embodiment of the present invention; FIG. 3B is a schematic diagram and a side view of structures of the turntable with multiple corona pins and the focusing electrode according to the embodiment of the present invention. A sealed metal shielding cylinder 305 is arranged inside the metal corona cylinder 300; and the metal corona cylinder 300 and the sealed metal shielding cylinder 305 are arranged coaxially. Preferably, the turntable 301 is contained in sealed metal shielding cylinder 305, and the metal shielding cylinders 305 include trumpet-shaped focusing electrodes 308 used for forming a gathered static electric field.

Preferably, a narrow slit 306 is formed on the focusing electrode 308, for pass of the corona pins 303 when rotating. The turntable 301 is driven by the rotating shaft 304 to expose a certain corona pin 303 from the narrow slit 306 by rotating (at this time, the corona pin is called a main corona pin), and to locate at a position matching with the electrode at ion exit of the corona cylinder 300 (the main corona pin is overlapped with the axial line of the corona cylinder 300 and the axial line of the trumpet-shaped opening of the focusing electrode 308, at this time, the pinpoint of the corona pin is closest to the ion exit of the corona cylinder 300), in order to generate corona discharge; the rest pins are contained in the metal shielding cylinders 305 with the same potential to fail to generate the corona discharge.

Preferably, the multiple corona pins 303 are electrically interconnected. By adopting the multiple electrically interconnected corona pins, respective current paths do not need to be singly provided for the multiple corona pins, so that the fabrication process is simplified; moreover, since expect the main corona pin, the rest corona pins are all located in the metal shielding cylinders 305, this arrangement will not cause the rest corona pins to generate unexpected corona discharge.

Preferably, the corona discharge assembly further includes an ion reaction and storage ring 320 which is an internal passage with a shape like a trumpet, wherein the ion reaction and storage ring 320 is not in electrical contact with the metal corona cylinders, and the large opening end of the ion reaction and storage ring 320 is in contact with a first grid 205 of an ion gate to form an equipotential area between the interior of the large opening end and the first grid 205 of the ion gate, in order to store ions. Therefore, the ions generated by corona discharge can enter an ion reaction and storage ring 320 under the traction of the electric field. The main functions of the ion reaction and storage ring are as follows: when the ion gate is closed, ensuring full reaction and compound between primary action ions and a sample gas and generating and storing a characteristic ion cluster to be detected; when the ion gate is open, focusing the compounded ion cluster and driving the ion cluster to enter an ion migration cavity through the ion gate. By means of the design, corona discharge impulse interference can be effectively shielded, the fluctuation of the number of the ions caused by corona impulse is shielded, the pass rate of the ions at the ion gate is increased, and an effect of stabilizing an ion mobility spectrum line is achieved.

When the ion mobility spectrometer is at work, the corona pins 303 have the same potential as the metal shielding cylinders 305, the voltage thereof is about 700-3000 V (determined by the radius of the tip of each corona pin and the length of each corona pin, different geometry sizes corresponding to different discharge inception voltages) higher than the voltage of the metal corona cylinder 300 to produce corona, in order to generate ions. The voltage of the ion reaction and storage ring 320 and a first ion gate 205 periodically hops, see FIG. 2B, it can be called a storage state (i.e., a full line part) when at a low voltage, and is called a traction state (i.e., a dotted line part) when at a corresponding high voltage. When the voltage of the ion reaction and storage ring 320 and the first ion gate 205 is at the storage state, the voltage is 60-150 V lower than the voltage of the metal corona cylinder 300 and is about 5-60V lower than the voltage of a second ion gate 206, after entering the first ion gate 205, the ions subject to weaker electric field force, and mainly perform thermal motion in the cavity of the first ion gate 205; after the ions in the first ion gate 205 are accumulated to a certain number over certain time, the voltage of the ion reaction and storage ring 320 and the first ion gate 205 hops to the traction state, at this time, the ions generated by corona at the corona pin 303 stop entering the first ion gate 205 (in order to prevent the fluctuation of the number of the ions in the first ion gate 205 caused by corona impulse), and the ions in the first ion gate 205 quickly enter the ion migration area 207 through the second ion gate 206 under the action of the electric field between the first ion gate 205 and the second ion gate 206. In the ion migration area 207 filled with a migration gas through a migration gas inlet (as shown on the right side in FIG. 2A), the ions achieve a symmetrical motion state under the coaction of electric field traction and reversely moving migration gas flow, after a long migration distance, the ions with different migration rates are separated due to different velocities and are finally collected by a Faraday disc 209 after passing by an inhibition grid 208 and are recorded by a rear end circuit. The gas in the ion mobility spectrometer is discharged from the gas outlet shown in the lower side of FIG. 2A.

The turntable 301 is fixed on a rotating shaft 304, and the rotating shaft 304 is installed on the wall of a metal corona cylinder 300 through an insulating sleeve 307. A rotating shaft handle (as shown by a rotating arrow in FIG. 3B) at the outside of a corona cavity is twisted, and the turntable 301 is driven by the rotating shaft 304 to rotate; multiple (preferably 4-8) corona pin mounting seats 302 are uniformly distributed on the turntable in a central symmetry manner, and all have the same potential, a jack is formed on each corona pin mounting seat 302, a corona pin 303 is welded in each jack, when rotating to a certain angle, one corona pin is located at the axle center of the corona cylinder 300 and is called a main corona pin; at the outside of the turntable 301, a metal shielding cylinder 305 with the same potential as the corona pin 303 is fixedly installed on the metal corona cylinder 300 through an insulating material, a vent hole 309 is formed in the gas inlet end of the metal shielding cylinder 305, a trumpet-shaped focusing electrode 308 is arranged at the other end thereof, the metal shielding cylinder 305 is used for shielding other corona pins to prevent forming a corona electric field with the corona cylinder 300, the trumpet-shaped focusing electrode 308 and an ion exit 310 of the corona cylinder form a gathered electric field, for enabling ions generated by corona discharge at the main corona to enter an ion reaction and storage ring 320 more easily, and reducing the loss caused by collision of the ions at the ion exit of the corona cylinder and the port of the ion reaction and storage ring, the conical shaft of the focusing electrode 308 characterizes by being overlapped with the axial line of the corona cylinder and the center shaft of the ion reaction and storage ring, has a field angle of 120-150 degrees, and the focusing electrode 308 and the corona pin 303 have the same potential. A narrow slit 306 is formed at a position crossing with the rotating plane of the corona pin of the turntable 301 on the metal shielding cylinder 305, for pass of the corona pin when rotating, the width of the narrow slit 306 cannot be too large and should be slightly larger than the diameter of the corona pin, thereby both ensuring the smooth pass of the corona pin 303 when rotating and avoiding damage to a focusing electric field at the narrow slit 306.

EXAMPLE

In the example, a specific design of a multi-pin turntable corona pin alternate discharge ion source assembly adopting a focusing structure is described. A focusing electrode 308 turntable multi-pin structure with 6 corona pins is as shown in FIG. 3A. The turntable 301 and the insulating sleeve 307 are made from polytetrafluoroethylene; the rotating shaft 304 is made from stainless steel; the corona pin mounting seat 302 is made from oxygen-free copper and a corona pin 303 is welded thereon by using a high temperature solder; the length stretching out from the mounting seat is 3 mm, the radius of a fillet at the pinpoint is 0.05 mm, and the pinpoint is ground by a metal platinum rod with a diameter of 0.5 mm; the metal shielding cylinder 305 is made from stainless steel, ridges at the two ends are rounded off to reduce the electric field intensity on the surface thereof, in order to avoid discharge, a trump-shaped vertex is 125 degrees, the stretched out corona pin 303 is located at the conical shaft of the focusing electrode 308 on the metal shielding cylinder 305, and the metal shielding cylinder 305 and the corona cylinder 300 are supported and fixed by a polytetrafluoroethylene insulating material. A narrow slit 306 with a width of 1 mm is formed at a position crossing with the rotating plane of the corona pin on the metal shielding cylinder 305.

According to an electric field analog computation result, see FIGS. 4A to 4D, when an opening voltage is applied to the ion gate, in a corona discharge structure without focusing electrode 308, the electric field at the pinpoint of the corona pin and the gas flow advance direction appoints to the ion exit of the corona cylinder 300, and the electric field direction in a part of areas in the ion reaction and storage ring points to the ring wall, thus it can be seen that a large number of ions generated at the pinpoint of the corona pin are lost by collision with the port 310 of the corona cylinder 300 and/or the inner wall of the ion reaction and storage ring; in a corona discharge structure with the focusing electrode 308, the electric field direction near the pinpoint and in the ion gas flow advance direction is parallel to the gas flow direction, and the electric field direction in the ion reaction and storage ring is basically parallel to the ion gas flow, this is conductive to enabling the ion gas flow to stably pass by the corona cylinder 300, to reduce collision dissipation and enable more ions to enter an ion migration area, so as to improve the sensitivity of the ion mobility spectrometer under the same corona discharge ionization intensity.

Due to the structural features of the corona discharge assembly according to the present invention, at any moment, only one corona pin rotates to the position closest to the ion exit of the corona cylinder 300, the electric field intensity at the pinpoint thereof reaches the corona discharge threshold to generate corona discharge, the rest pins do not discharge because the electric field intensity at the pinpoints thereof fails to reach the corona discharge threshold, the multiple pins alternatively locate at a corona discharge position to discharge due to the rotation of the turntable, thus compared with a single-pin structure, the structure can be used for prolonging the service life of the integral corona discharge assembly; meanwhile, due to the focusing function of the focusing electrode 308, the ion pass rate can be increased, the dissipation of the ions in the corona cylinder 300 and the ion reaction and storage ring is reduced, more ions generated within a unit time can enter the ion migration area; the sensitivity of the ion mobility spectrometer is beneficially improved; since the multiple corona pins are fixed on the turntable, during installation, the position of the electrode can be accurate and stable, thus mass manufacture is easier to achieve.

According to the embodiment of the present invention, a computer program for corona discharge assembly is further disclosed. In order to control corona discharging of the corona discharge assembly, the computer program comprises the following step: wherein, at any moment, only one corona pin rotates to the position closest to the ion exit of the corona cylinder 300, the electric field intensity at the pinpoint thereof reaches the corona discharge threshold to generate corona discharge, the rest pins do not discharge because the electric field intensity at the pinpoints thereof fails to reach the corona discharge threshold, the multiple pins alternatively locate at a corona discharge position to discharge due to the rotation of the turntable.

According to the embodiment of the present invention, a computer readable storage medium for storing the computer program above.

Based on above contents, compared with a single-pin structure, corona discharge assembly, the ion mobility spectrometer, the computer program and the computer readable storage medium according to the present invention can be used for prolonging the service life of the integral corona discharge assembly; meanwhile, due to the focusing function of the focusing electrode 308, the pass rate of the ions can be increased, the dissipation of the ions in the corona cylinder 300 and the ion reaction and storage ring is reduced, more ions generated within a unit time can enter the ion migration area; the sensitivity of the ion mobility spectrometer is beneficially improved; since the multiple corona pins are fixed on the turntable, during installation, the position of the electrode can be accurate and stable, thus mass manufacture is easier to achieve.

The present invention can be implemented in any suitable form, including hardware, software, firmware or any combination thereof. Optionally, the present invention can be at least partially implemented as computer software running on one or multiple data processors and/or digital signal processors. The elements and components in the embodiment of the present invention can be physically, functionally and logically implemented in any suitable form. In fact, the functions can be implemented in a single unit, in multiple units or as a part of other functional units. Similarly, the present invention can be implemented in a single unit or can be physically and functionally distributed between different units and processors.

Although the present invention has been described in combination with some embodiments, the present invention is not intended to be limited to the specific form set forth herein. On the contrary, the scope of the present invention is only limited by the appended claims. Additionally, although the features may appear to be described in combination with particular embodiments, those skilled in the art should recognize that the various different features of the described embodiments can be combined according to the present invention. In the claims, the wording including/containing does not exclude the presence of other elements or steps.

Furthermore, although individually listed, a plurality of devices, elements or method steps can be implemented by, for example, a single unit or a processor. Additionally, although the individual features can be included in different claims, these features can be combined advantageously, and its inclusion in different claims does not imply that the combination of the features is not feasible and/or advantageous. In addition, the inclusion of the features in a claim category does not imply it is limited to this category, but indicates that the features can be suitably applied to other claim categories as well. Furthermore, the sequence of the features in the claims does not imply any specific sequence in which the features must work.

Industrial Applicability

The corona discharge assembly, the ion mobility spectrometer, the computer program and the computer readable storage medium according to the present invention can keep only one corona pin rotates to the position closest to the ion exit of the corona cylinder at any moment, the electric field intensity at the pinpoint thereof reaches the corona discharge threshold to generate corona discharge, the rest pins do not discharge because the electric field intensity at the pinpoints thereof fails to reach the corona discharge threshold, the multiple pins alternatively locate at a corona discharge position to discharge due to the rotation of the turntable, thus compared with a single-pin structure, the structure can be used for prolonging the service life of the integral corona discharge assembly; meanwhile, due to the focusing function of the focusing electrode, the pass rate of the ions can be increased, the dissipation of the ions in the corona cylinder and the ion reaction and storage ring is reduced, more ions generated within a unit time can enter the ion migration area; the sensitivity of the ion mobility spectrometer is beneficially improved; since the multiple corona pins are fixed on the turntable, during installation, the position of the electrode can be accurate and stable, thus mass manufacture is easier to achieve.

The invention claimed is:

1. A corona discharge assembly, characterized in that, the corona discharge assembly comprises:
   an ionization discharge chamber, wherein the ionization discharge chamber comprises a metal corona cylinder, and the metal corona cylinder is provided with an inlet of a gas to be analyzed and an ion exit which forms a non-uniform electric field with corona pins and is provided with a circular hole at the middle;
   a rotating shaft is installed on the cylinder wall of the metal corona cylinder in an insulating manner, the rotating shaft is orthogonal and vertical to the longitudinal axial line of the metal corona cylinder, and
   a turntable provided with multiple corona pins at the outer edge is installed at the end part of the rotating shaft, the longitudinal axial line of the metal corona cylinder passes in parallel through the rotation plane of the turntable.

2. The corona discharge assembly according to claim 1, characterized in that, a sealed metal shielding cylinder is arranged inside the metal corona cylinder, the turntable is contained in a sealed metal shielding cylinder, and the metal shielding cylinder includes a trumpet-shaped focusing electrode used for forming a gathered static electric field;
   the corona pin generating corona discharge is stretched into the focusing electrode.

3. The corona discharge assembly according to claim 2, characterized in that, the metal corona cylinder and the sealed metal shielding cylinder are arranged coaxially.

4. The corona discharge assembly according to claim 3, characterized in that, the corona pin is located at the conical shaft of the focusing electrode.

5. The corona discharge assembly according to claim 3, characterized in that, a narrow slit is formed on the focusing electrode, for pass of the corona pins when rotating.

6. The corona discharge assembly according to claim 1, characterized in that, the multiple corona pins are electrically interconnected.

7. The corona discharge assembly according to claim 1, characterized in that, the corona discharge assembly further comprises an ion reaction and storage ring which is an internal passage with a shape like a trumpet, wherein the ion reaction and storage ring is not in electrical contact with the metal corona cylinder, and the large opening end of the ion reaction and storage ring is in contact with a first grid of an ion gate to form an equipotential area between the interior of the large opening end and the first grid of the ion gate, in order to store ions.

8. An ion mobility spectrometer, characterized in that, the ion mobility spectrometer comprises:
   the corona discharge assembly according to claim 1;
   an ion gate, wherein the ion gate is composed of two opposite grids;
   a migration area, wherein the migration area comprises drift electrodes, and the drift electrodes are concentric equidistant circular ring electrodes; and
   a Faraday disc, wherein the rear of the Faraday disc is connected with a charge sensitive amplifier to read ion signals.

9. A method for performing corona discharge by using the corona discharge assembly according to claim 1, wherein at any moment, only one corona pin rotates to the position closest to an annular piece-shaped port of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, and the multiple pins alternatively locate at a corona discharge position to discharge due to the rotation of the turntable.

10. A non-transitory computer readable storage medium storing a computer program for controlling corona discharging of the corona discharge assembly according to claim 1, wherein the computer program comprises the following operations:
   at any moment, only one corona pin rotates to the position closest to the ion exit of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, and the multiple pins alternatively locate at a corona discharge position to discharge due to the rotation of the turntable.

11. A method for performing corona discharge by using the corona discharge assembly according to claim 2, wherein at any moment, only one corona pin rotates to the position closest to an annular piece-shaped port of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, and the multiple pins alternatively locate at a corona discharge position to discharge due to the rotation of the turntable.

12. A method for performing corona discharge by using the corona discharge assembly according to claim 3, wherein at any moment, only one corona pin rotates to the position closest to an annular piece-shaped port of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, and the multiple pins alternatively locate at a corona discharge position to discharge due to the rotation of the turntable.

13. A method for performing corona discharge by using the corona discharge assembly according to claim 4, wherein at any moment, only one corona pin rotates to the position closest to an annular piece-shaped port of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, and the multiple pins alternatively locate at a corona discharge position to discharge due to the rotation of the turntable.

14. A method for performing corona discharge by using the corona discharge assembly according to claim 5, wherein at any moment, only one corona pin rotates to the position closest to an annular piece-shaped port of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, and the multiple pins alternatively locate at a corona discharge position to discharge due to the rotation of the turntable.

15. A method for performing corona discharge by using the corona discharge assembly according to claim 6, wherein at any moment, only one corona pin rotates to the position closest to an annular piece-shaped port of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, and the multiple pins alternatively locate at a corona discharge position to discharge due to the rotation of the turntable.

16. A method for performing corona discharge by using the corona discharge assembly according to claim 7, wherein at any moment, only one corona pin rotates to the position closest to an annular piece-shaped port of the corona cylinder, the electric field intensity at the pinpoint thereof reaches the corona discharge threshold to generate corona discharge, the rest pins do not discharge because the electric field intensity at the pinpoints thereof fails to reach the corona discharge threshold, and the multiple pins alternatively locate at a corona discharge position to discharge due to the rotation of the turntable.

* * * * *